United States Patent [19]

Fern et al.

[11] 4,153,624

[45] May 8, 1979

[54] PREPARATION OF ORGANIC ISOCYANATES

[75] Inventors: William A. Fern; Philip A. B. Rodriguez, both of Blackley, England

[73] Assignee: Imperial Chemical Industries Limited, London, England

[21] Appl. No.: 873,953

[22] Filed: Jan. 31, 1978

[30] Foreign Application Priority Data

Feb. 3, 1977 [GB] United Kingdom ............... 4452/77

[51] Int. Cl.$^2$ ............................................. C07C 118/00
[52] U.S. Cl. ............................. 260/453 P; 260/553 C

[58] Field of Search ...................................... 260/453 P

[56] References Cited

U.S. PATENT DOCUMENTS 3,465,025  9/1969  Brownstein et al. ............ 260/453 P

*Primary Examiner*—Dolph H. Torrence
*Attorney, Agent, or Firm*—Cushman, Darby & Cushman

[57] ABSTRACT

A process for the manufacture of organic isocyanates which comprises reacting a substituted urea having at least one unsubstituted NH$_2$ group with nitrous acid in the presence of a water-immiscible solvent and a phase transfer agent.

7 Claims, No Drawings

PREPARATION OF ORGANIC ISOCYANATES

This invention relates to the manufacture of organic isocyanates from substituted ureas by treatment with nitrous acid in the presence of a water immiscible solvent and a phase transfer catalyst.

Organic isocyanates are in general manufactured by the phosgenation of primary amines but this process presents a severe toxic hazard due to the use of phosgene. Furthermore, small scale manufacture of isocyanates can be expensive because of phosgene handling costs. Other methods of manufacturing organic isocyanates have been proposed although none have so far been commercially attractive. One of these methods is the reaction of a substituted urea with nitrous acid in the presence of an apolar solvent, which is described in La Chimica et L'Industria 1960, 42, 1243.

We have now found that higher yields may be obtained using this method if a phase transfer catalyst is incorporated in the reaction mixture.

Thus according to the present invention there is provided a process for the manufacture of organic isocyanates which comprises reacting a substituted urea having at least one unsubstituted $NH_2$ group with nitrous acid in the presence of a water-immiscible solvent and a phase transfer agent.

Substituted ureas which may be used include ureas of the formula $RNHCONH_2$ wherein R is an optionally substituted alkyl, cycloalkyl, aralkyl or aryl group. It will be realized that any substituent present must be non-reactive towards an isocyanate group.

Examples of R include ethyl, propyl, iso-propyl, n-butyl, tert-butyl, 2-ethylhexyl, dodecyl, cetyl, cyclohexyl, benzyl, α-phenylethyl, α-phenylpropyl, β-phenylpropyl, diphenylmethyl, phenyl, p-chlorophenyl, 3,4-dichlorophenyl, o-, m- and p-tolyl, and other substituted phenyl radicals with substituents which do not react readily with the isocyanate group under the conditions employed.

The process of the invention is particularly valuable when R is an alkyl group of 2 to 10 carbon atoms.

There may also be used in the invention bis-ureas in which each of the urea groups is monosubstituted for example bisureas of the formula $NH_2CONH-R^1-NHCONH_2$ where $R^1$ is a divalent aliphatic or aromatic radical.

Examples of $R^1$ include hexamethylene and 2,4-tolylene.

Nitrous acid for use in the reaction may be generated in situ in the reaction mixture by any of the well known methods for example by interaction between sodium nitrite and hydrochloric acid. This may be done for example by adding an aqueous solution of sodium nitrite and concentrated hydrochloric acid. The amount of water used should preferably be kept to a low level.

Examples of water-immiscible solvents which may be used include hydrocarbons for example benzene, toluene and petroleum ethers, chlorinated hydrocarbons for example methylene dichloride, chloroform, chlorobenzenes and chlorotoluenes, esters for example ethyl and butyl acetates, nitrated benzenes such as nitrobenzenes.

Small amounts of water-miscible solvents may be incorporated in the reaction mixture to assist solubility of the urea providing that the amount used does not affect the separation of the water-immiscible solvent and the aqueous layer and the solvent does not dissolve extensively in the aqueous layer. Examples of such solvents include ethers for example 1,2-dimethoxyethane, acetonitrile and dimethylsulphoxide. Any solvent used should be non-reactive to the isocyanate group.

The expression "phase transfer agent" used herein means a substance which promotes reaction by transferring a reactant together with itself from a first phase to a second phase where reaction takes place thereby releasing the phase transfer agent back into the first phase for re-use. Phase transfer agent are reviewed by E. V. Dehmlow in Angewandte Chemie (International Edition) Vol. 13, No. 3, pages 170-178, 1974.

Preferably, the phase transfer agent used in the process of the invention is a quaternary salt of the formula:

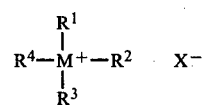

wherein M is a pentavalent element of Group V of the periodic table, especially nitrogen or phosphorus, $R^1$, $R^2$, $R^3$ and $R^4$ represent organic radicals and $X^-$ represents an anion. Organic radicals which may be represented by $R^1$, $R^2$, $R^3$ and $R^4$ include optionally substituted alkyl, alkenyl, aryl, aralkyl and cycloalkyl radicals or, alternatively, at least two of $R^1$, $R^2$, $R^3$ and $R^4$ may be joined or fused together to form rings. Anions which may be represented by $X^-$ include, in particular, chloride, bromide, fluoroborate and methosulphate ions. Double or multifunctional quaternary salts in which the formula $(R^1R^2R^3R^4M^+)X^-$ is repeated a plurality of times may also be used. The preferred phase transfer catalysts are quaternary ammonium salts in which $R^1$, $R^2$ and $R^3$ are alkyl radicals and $R^4$ is alkyl or aralkyl, the four radicals taken together containing at least 12 and preferably 16-30 carbon atoms. As examples of suitable quaternary salts, there may be mentioned cetyltrimethylammonium bromide, benzyltri-n-butylammonium chloride, cetyltrimethylammonium chloride, cetyltri-n-propylphosphonium bromide, octyltributylammonium bromide, tetrabutyl ammonium bromide, trioctylmethylammonium chloride, benzyldimethyllauryl ammonium chloride and tetrabutylammonium sulphate.

If desired, the quaternary salt may be formed in situ, for example by including a tertiary amine and an alkylating agent in the reaction mixture.

Other phase transfer catalysts which may be used include crown ethers (macrocyclic polyesters) which are described in the Journal of the American Chemical Society, Vol. 89, pages 7017-7036, 1967 by C. J. Pedersen.

The phase transfer agent is used in a catalytically effective amount, suitably in an amount of from 0.1% to 50% preferably 1% to 20% by weight of the urea.

The process of the invention is conveniently carried out by mixing the urea, water-immiscible solvent and phase transfer catalyst and adding sodium nitrite and hydrochloric acid to the above mixture slowly over a period of time, for example from two to ten hours.

It is convenient to use an excess of nitrous acid in respect of the urea, preferably from 1.5 to 2.5 moles of nitrous acid per mole of urea. In the case of a bis-urea this becomes 3.0 to 5.0 moles of nitrous acid per mole of bis-urea.

The isocyanate may be isolated at the end of the reaction by separation of the solvent layer from the aqueous layer followed by distillation of the solvent and finally the isocyanate.

It is not absolutely necessary to isolate the isocyanate as we have found that the solvent solution of isocyanate produced may be used advantageously for on-going reactions to produce derivatives of the isocyanate such as urethanes and amides.

Isocyanates produced by the present process are useful for the manufacture of urethanes and amides which are useful as agricultural and pharmaceutical chemicals.

The invention is illustrated by the following examples in which all parts and percentages are by weight except where otherwise stated.

EXAMPLE 1

Preparation of tert-butyl isocyanate

A multinecked flask was fitted with stirrer, thermometer, charging funnel and condenser. Tert-butyl urea 14.5 parts was charged to the reaction flask followed by solvent, toluene 64.5 parts and 1.45 parts tetra-n-butyl ammonium bromide. The slurry obtained was cooled to below 5° C. and stirred at this temperature until all the tert-butyl urea had gone into solution.

A solution of sodium nitrite 18 parts in water 25 parts was added to the reaction flask concurrently with a charge of concentrated HCl 25 parts over a period of seven hours.

At the end of the addition a 5 ml sample was removed and the NCO value determined using di-n-butylamine. The total wt. of product obtained was calculated from this value.

Yield = 10 parts
% Yield = 81%

EXAMPLE 2 (COMPARATIVE)

Preparation of tert-butyl isocyanate

Similar experiment to Ex. 1 except that no phase transfer agent was added to the reaction mixture. The addition of the NaNO₂/HCl was reduced from 7 hrs. to 5 hours and also the amount of conc. HCl was increased from 25 parts to 27.5 parts i.e. 10%.

Yield = 7.6 parts
% Yield = 61.6

EXAMPLE 3

Preparation of n-butyl isocyanate

Carried out as Example 1 except that addition of NaNO₂/HCl took six hours. Using 10% loading of tetra-n-butyl ammonium bromide. Chloroform used in place of toluene.

Yield = 10.4 parts
% Yield = 86.2

A similar experiment omitting the phase transfer agent gave a yield of 9.1 parts (73.00%).

EXAMPLE 4

Preparation of Ethyl isocyanate

Carried out as Example 3 using ethyl urea in place of n-butyl urea.

Yield = 4.3 parts
% Yield = 48.0
Without phase transfer agent.
Yield = 3.4 parts
% Yield = 38.4

EXAMPLE 5

Preparation of Propyl isocyanate

Carried out as Example 3 using propyl urea.
Yield = 9.1 parts
% Yield = 85.2
Without phase transfer agent
Yield = 7.5 parts
% Yield = 71

EXAMPLE 6

Preparation of Allyl isocyanate

Carried out as Example 3 using allyl urea.
Yield = 7.5 parts
% Yield = 72.1
Without phase transfer agent.
Yield = 7.0 parts
% Yield = 67.3

EXAMPLE 7

Preparation of Benzyl isocyanate

Carried out as Example 3 using benzyl urea.
Yield = 14.2 parts
% Yield = 85
Without phase transfer agent.
Yield = 12.8 parts
% Yield = 76.5

EXAMPLE 8

Preparation of Phenyl isocyanate using mixed solvent

Carried out as Example 1 using phenyl urea and except that mixed solvents used to increase the solubility of the phenyl urea in the solvent system. Used chloroform 96 parts and 1,2-dimethoxyethane 14 parts.
Yield = 11.9 parts
% Yield = 80
Without phase transfer agent.
Yield = 9.0 parts
% Yield = 60

In this and preceding examples carried out by the method of Examples 1 and 3 the amount of the respective urea used was adjusted to take account of the molecular weight.

EXAMPLE 9

Preparation of hexamethylene diisocyanate (a) Without phase transfer agent.

N,N'-hexamethylene bis-urea (5.05 parts) and a solution of sodium nitrite (6.9 parts) in water (10 parts) were added over 6 hours to a mixture of chloroform (130 parts) and conc. hydrochloric acid (10.3 parts) at −10° C. to −5° C. Then filtered and a 5 mls. sample removed for analysis. The content of diisocyanate was determined by gas liquid chromatography using an internal standard.

Wt. Hexamethylene diisocyanate 0.13 parts
% Yield 3.1%

(b) With phase transfer agent

As above, but with 10% tetra-butyl ammonium fluoroborate added.

Wt. Hexamethylene diisocyanate 0.26 parts
% Yield 6.2%

EXAMPLE 10

(A) Preparation of 4-chlorophenyl isocyanate

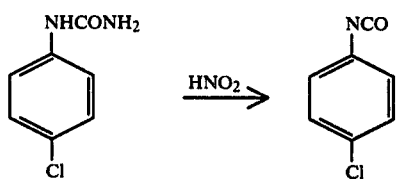

4-Chlorophenyl urea (8.5 parts) and a solution of sodium nitrite (6.9 parts) in water (10 parts) were added over 6 hours to a mixture of conc. hydrochloric acid (10.3 parts) chloroform (130 parts) and tetra-n-butyl ammonium fluoroborate (10% by weight based on 4-chlorophenyl urea) at $-10°$ to $-5°$ C. The mixture was stirred for a further 15 minutes then the stirrer stopped and layers allowed to separate. No solid was present at this stage. 5 mls of the organic layer was taken for analysis and the remainder kept cold until required.

Wt. Product 7.7 parts
% Yield 100%

Similar experiments carried out with different amounts of phase transfer agent (PTA) gave the following results:

| 2.5% | PTA | Yield | 54.4% |
|------|-----|-------|-------|
| 5.0% | PTA | Yield | 78.2% |
| No | PTA | Yield | 44.8% |

(B) Conversion to Trichlorocarbanilide

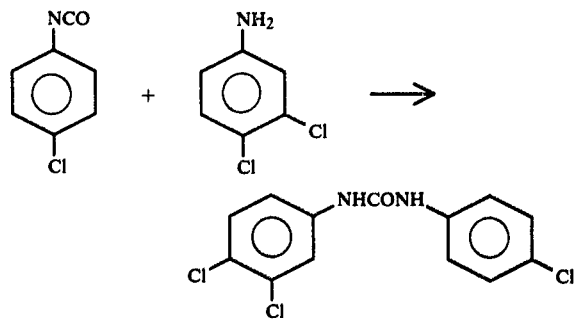

A cold solution of 3,4-dichloroaniline (13.2 parts) in chloroform 75 parts was added to the isocyanate solution from A (120 parts containing 7.5 parts of 4-chlorophenyl isocyanate). The mixture was stirred at room temperature for 16 hours, then the solid filtered off, washed with chloroform and dried.

Wt. 11.2 parts
mpt 240°–245°
Yield 76.7%

(C) Example 10A was repeated using as phase transfer agent, benzyl trimethyl ammonium bromide (10% by weight of the urea) in place of tetra-n-butyl ammonium fluoroborate, the yield of 4-chlorophenyl isocyanate was 74.5% of theory.

EXAMPLE 11

Preparation of 3,4-dichlorophenyl isocyanate

As Example 8, but using chloroform (80 parts) and dimethoxyethane (25 parts) with 10% tetra-n-butylammonium fluoroborate and the appropriate amount of 3,4-dichlorophenyl isocyanate.

Wt. Isocyanate 7.7 parts
% Yield = 81.6%
Without the phase transfer agent present.
Wt. Isocyanate 3.2 parts
% Yield = 35.8%.

The above example was repeated using the following phase transfer agents, the yield of 3,4-dichlorophenyl isocyanate being given in each case.

(a) Benzyl trimethyl ammonium chloride: 64.4% yield
(b) Benzyl lauryl dimethyl ammonium chloride: 44.0%
(c) Benzyl trimethyl ammonium bromide: 71.4%

We claim:

1. A process for the manufacture of an organic isocyanate which comprises reacting a substituted urea of the formula:

$$RNHCONH_2$$

wherein R is an alkyl, aralkyl or aryl group or is phenyl substituted with a substituent which does not react with the isocyanate group under the process conditions employed; or a substituted urea of the formula:

$$H_2NCONHR^1NHCONH_2$$

wherein $R^1$ is hexamethylene or 2,4-tolylene; with nitrous acid in the presence of a water-immiscible solvent and a phase transfer agent.

2. A process as claimed in claim 1 wherein the phase transfer agent has the formula:

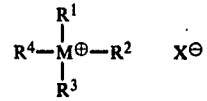

wherein M represents nitrogen or phosphorus, $R^1$, $R^2$ and $R^3$ are alkyl radicals and $R^4$ is alkyl or aralkyl, the four radicals together containing 16 to 30 carbon atoms, and X is an anion.

3. A process as claimed in claim 1 wherein R is an alkyl group of 2 to 10 carbon atoms.

4. A process as claimed in claim 2 wherein M represents nitrogen.

5. A process as claimed in claim 1 wherein the phase transfer agent is used in an amount of from 0.1% to 50% by weight of the substituted urea.

6. A process as claimed in claim 1 wherein the phase transfer agent is used in an amount of from 1% to 20% by weight of the urea.

7. A process as claimed in claim 1 wherein there is used from 1.5 to 2.5 moles of nitrous acid per mole of substituted urea or from 3.0 to 5.0 moles if the substituted urea is a bis-urea.

* * * * *